United States Patent [19]

D'Antonio

[11] 4,272,249
[45] Jun. 9, 1981

[54] METHOD OF MONITORING OXYGEN CONCENTRATIONS IN GAS STREAMS

[75] Inventor: Joseph P. D'Antonio, Woodbury, Conn.

[73] Assignee: E. I. Du Pont de Nemours and Company, Wilmington, Del.

[21] Appl. No.: 115,756

[22] Filed: Jan. 28, 1980

[51] Int. Cl.³ .......................................... G01N 21/76
[52] U.S. Cl. .................... 23/232 E; 23/927; 422/52
[58] Field of Search ........... 422/52; 23/232 R, 232 E, 23/DIG. 927; 356/246

[56] References Cited

U.S. PATENT DOCUMENTS

| 2,389,046 | 11/1945 | Hare | 23/232 R |
|---|---|---|---|
| 3,528,779 | 9/1970 | Fontijn | 23/232 E |
| 3,718,429 | 2/1973 | Williamson, Jr. | 23/232 R |
| 3,970,430 | 7/1976 | Reader, Jr. et al. | 23/232 R |
| 4,042,333 | 8/1977 | Dell et al. | 23/232 R |

OTHER PUBLICATIONS

An Optical Detection Method for NO in the Range of $10^{-2}$ to $10^3$ ppm by the Chemiluminescent Reaction of NO with $O_3$.
Stuhl et al., Tech. Rep. No. SR-70-42, Mar. 23, 1970.
"461 $NO_x$ Analyzer System", (Du Pont).

Primary Examiner—Michael S. Marcus

[57] ABSTRACT

The concentration of oxygen in a gas stream is determined by passing the gas stream through an optical absorption cell maintained above about 100° C., sealing off the cell, injecting sufficient amount of nitrogen oxide, NO, to react with all of the oxygen in the gas stream, and determining the absorbance of nitrogen dioxide, $NO_2$, formed in that reaction. This method is quick, accurate, and independent of gas flows or gas pressure.

7 Claims, 2 Drawing Figures

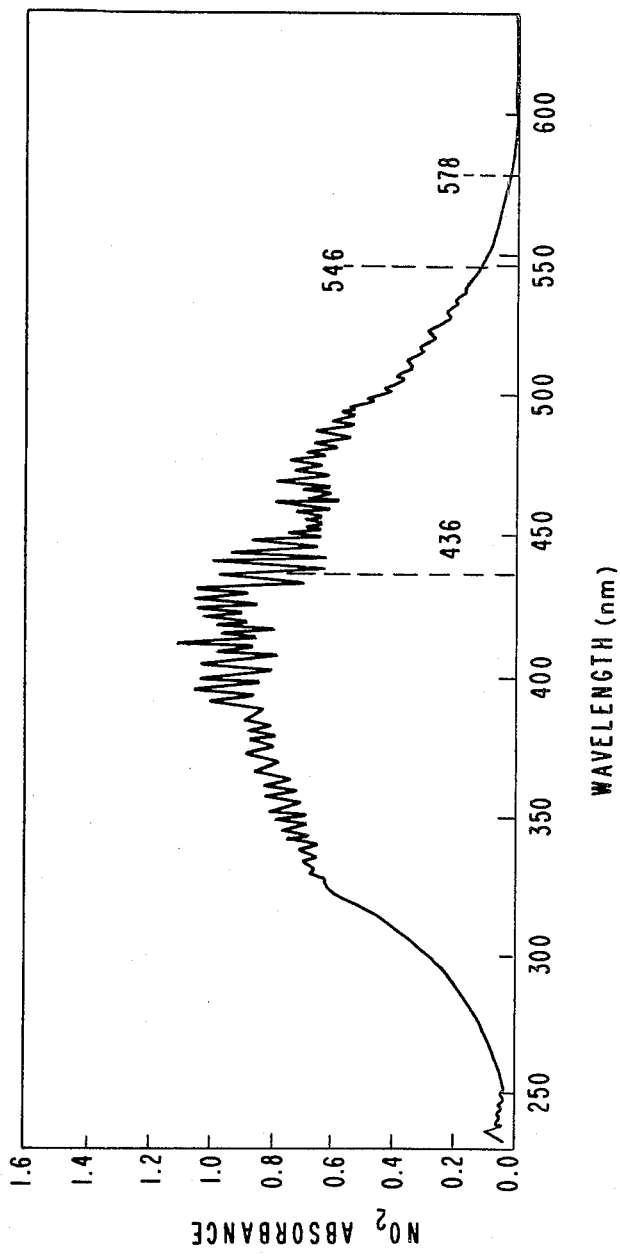

METHOD OF MONITORING OXYGEN CONCENTRATIONS IN GAS STREAMS

BACKGROUND OF THE INVENTION

This invention is directed to an analytical method which permits quick and accurate repetitive determinations of oxygen concentrations in gas streams.

Oxygen often is found in gaseous emissions from various industrial processes, especially those involving combustion, as well as in some chemical process off-gases, whenever air is injected into the process stream. Although the presence of oxygen in those emissions is not considered harmful to the environment, air acts as a diluent for various pollutants present in those emissions so that it is impossible to ascertain compliance with environmental control regulations unless this dilution level can be accurately determined. It thus is necessary to be able to accurately monitor the level of oxygen in gaseous industrial emissions. An accurate measurement of oxygen level is also invaluable for combustion control. A typical source of gas emissions is a refinery stack, the concentration of oxygen in stack gases being anywhere from negligible to as much as 20% by volume or more.

Various oxygen monitoring devices are commercially available. For example, an electrochemical device based on zirconium oxide can be used, but it has the drawback of requiring an operating temperature of at least 700° C., above the ignition point of most combustible gases, such as refinery gases. This requires isolation of the device in an explosion-proof box, which adds to the bulk, cost, and inconvenience.

Another oxygen-monitoring method is based on paramagnetic property measurements. This operation is carried out at a room temperature, so that it is necessary to use complicated sampling systems to avoid errors due to moisture condensation.

Other methods rely on color changes of solutions wherein the active component undergoes oxidation from a leuco form to a colored form. Such reactions, although well known and routinely used in oxygen analysis, are not practical for rapid and repetitive oxygen determination.

A rapid and possibly useful method of monitoring oxygen concentrations in gas streams is described in U.S. Pat. No. 2,389,046 to D. G. C. Hare, granted in 1945. According to that disclosure, a gas sample is diverted and continuously passed through two optical cells illuminated by the same light source. Nitric oxide is introduced into one of the cells in sufficient amount to react with all of the oxygen in the gas sample, at least some of the reaction product being "the red nitrogen tetroxide, $N_2O_4$." The intensities of light transmitted by the optical cells are continuously detected by two photoelectric cells connected in a bridge circuit, and the difference is measured by a galvanometer. This method is said to require only 5 to 10 seconds for a complete color development.

It is believed that the patentee actually measures the light absorption due to nitrogen dioxide, $NO_2$, rather than tetroxide, $N_2O_4$, which is known to be colorless. However, assuming good calibration of the equipment and maintenance of constant flows and temperature, there is no reason why this method should not be able to function satisfactorily. However, it has not found wide acceptance in the industry. The main reasons for this are believed to be as follows: The gas flows of the sample, and of nitrogen oxide, NO, must be known and controlled exactly because NO acts as a diluent for the gas sample to which it is added, and the galvanometer reading must be corrected for this dilution. Since the rate of reaction (1), above, is very much temperature dependent (the rate decreasing with increasing temperatures), it is important to control the operating temperature closely in view of the short residence time in the optical cells. It is necessary to maintain carefully controlled, constant gas flows, both because the calibration depends on the gas flows and because the gas flows of the gas sample in both cells must be identical in order to eliminate the background effect.

Therefore, a sample and reliable method for monitoring oxygen concentrations at moderate temperatures, capable of providing accurate results in a short time, is very desirable.

SUMMARY OF THE INVENTION

According to this invention, there is now provided a method of monitoring oxygen concentrations in a gas mixture, said method comprising the following steps:

(1) passing at a predetermined pressure a sample of the gas to be analyzed through a leak-tight optical absorption cell having high transparency in the 325–600 nm range and maintained at a predetermined temperature above 100° C., said optical absorption cell being placed in the path of a visible light beam;

(2) sealing off said optical absorption cell at said predetermined pressure;

(3) establishing by means of a light detector the base absorbance of the gas to be analyzed or zeroing the light detector to eliminate said base absorbance;

(4) introducing into said optical absorption cell nitrogen oxide, NO, at a pressure at least equal to twice the partial pressure of oxygen in the gas sample;

(5) determining the absorbance, at a predetermined wavelength within the 325–600 nm range, of nitrogen dioxide, $NO_2$, formed by reaction of oxygen with nitrogen oxide, NO; and (6) calculating the oxygen concentration in the gas sample from said absorbance;

with the proviso that the above step (3) may be performed at any time prior to the introduction of nitrogen oxide into the optical absorption cell, whether or not the cell is sealed off.

BRIEF DESCRIPTION OF THE DRAWINGS

FIG. 2 is a plot of wavelength vs. absorbance of nitrogen dioxide, $NO_2$.

DETAILED DESCRIPTION OF THE INVENTION

Figure 1:
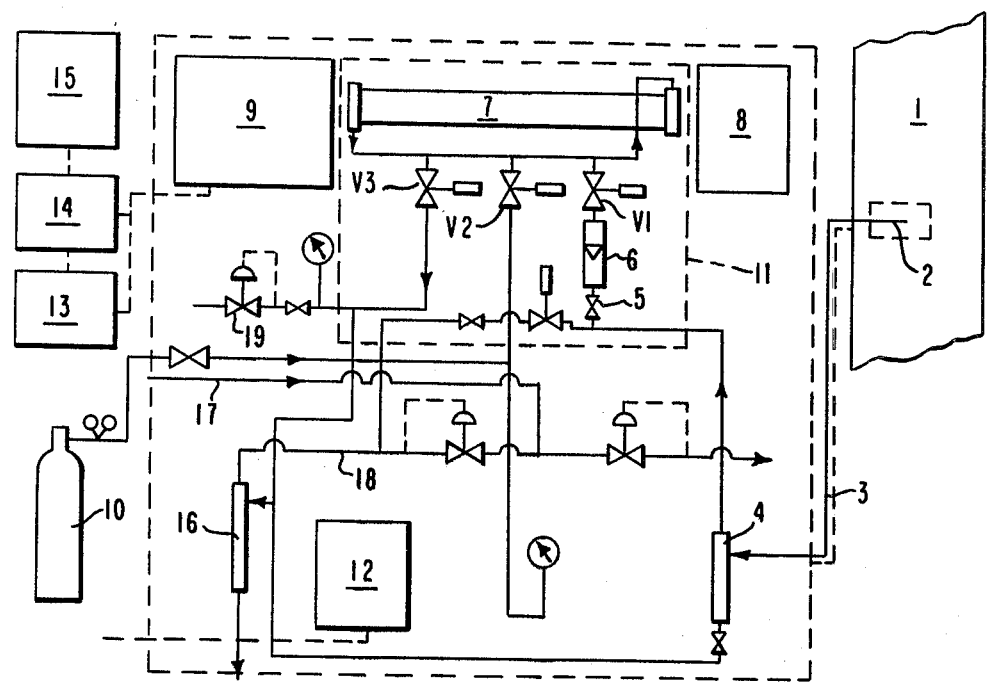
FIG. 1 is a block diagram of an apparatus suitable for carrying out the process of this invention.

The colorimetric method of oxygen analysis according to the present invention is based on the chemical reaction shown below in equation (1):

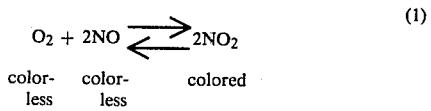

(1)

At temperatures below 100° C. some or all of $NO_2$ may dimerize to the colorless nitrogen tetroxide, $N_2O_4$, as shown in equation (2):

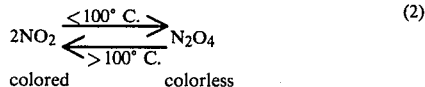

$$2NO_2 \underset{>100°\,C.}{\overset{<100°\,C.}{\rightleftarrows}} N_2O_4 \qquad (2)$$

colored    colorless

Because dimerization of $NO_2$ to $N_2O_4$ would reduce the absorbance of the gas mixture and could lead to incorrect results, an operating temperature of at least 100° C. is required. A practical temperature is about 105° C. Naturally, the gas sample should be at about the same temperature at the point of its introduction into the optical cell. This can be accomplished by either heating or cooling the gas sample lines, as the case may be.

It can be seen from equation (1), above, that two molecules of NO are required for one molecule of oxygen. Because this is a reversible reaction, it is advisable to have an excess of NO. A practical amount of NO would be a 100% excess, which means that the partial pressure of $NO_2$ in the cell would be about four times that of oxygen. The latter can be roughly estimated or determined for a given process or given conditions ahead of time by any conventional method. The pressure at which NO is introduced into the cell will usually lie in the 0.01 to 0.2 MPa range. Contrary to the method of U.S. Pat. No. 2,389,046, it is not necessary for the calculation of oxygen concentration to know the exact amount of NO or $NO_2$ in the cell, nor is the accuracy of the results affected by the total gas pressure in the cell at the time of absorbance reading. It is sufficient to know the pressure at which the optical cell has been sealed off. In practice, it is sufficient that the pressure at which the optical cell has been sealed off is the same as that for which the cell has been calibrated, as discussed below.

While various light detecting devices can be used, it is practical to use a photometer because of its ruggedness and simplicity. A convenient apparatus for the practice of the present invention is available from E. I. du Pont de Nemours and Company, Wilmington, Delaware 19898, U.S.A., under the designation "461 $NO_x$ Analyzer System," which is described in Du Pont sales literature as well as in U.S. Pat. No. 3,718,429 to J. A. Williamson, Jr.

Referring to FIG. 1, which shows the basic components of the "461" system, a gas sample is removed by filter probe 2 from source 1 and transferred through optionally heated tubing 3, via liquid condensation trap 4, flow controller 5, rotameter 6, and ball valve V1 to optical cell 7. Source 1 may be, for example, a smokestack or industrial process vent. Optical cell 7 is leak-tight and capable of withstanding superatmospheric pressures, for example, 0.2-0.5 MPa. The optical cell 7 is preferably made of metal such as, for example, stainless steel, and has quartz windows. The cell length may vary but usually will be about 38 cm and its internal diameter about 2.5 cm. Cell 7 is placed in the path of a visible light beam from source 8, which travels to photometer 9, where it is detected. Optical cell 7 is sealed off by closing ball valves V1 and V3, and NO is introduced from cylinder 10 through ball valve V2. Optical cell 7, together with its associated piping, ball valves V1, V2, and V3, and rotameter 6, is enclosed in heated chamber 11, maintained at about 105° C. After absorbance of the gas mixture has been determined by photometer 9, the optical cell is purged by opening valve V3 and again introducing the gas to be analyzed through valve V1. Power supply 12 powers light source 8, photometer 9, and remote control ball valves V1, V2, and V3. The time cycle for those ball valves is controlled by timer 13. Control station 14 ascertains that the system operates according to the preset conditions. Recorder 15 records plots of gas mixture's absorbance. It is usually preferred, but not required, to operate at a subatmospheric pressure. Subatmospheric pressure is maintained in optical absorption cell 7 by means of aspirator 16, which operates on air injected through lines 17 and 18. Vacuum breaker 19 controls the pressure, which is preferably set at about 0.06 MPa. The complete cycle from optical absorption cell purge through sealing, introduction of NO, and absorbance reading is about 2 minutes.

A mercury vapor lamp is used as the light source. The light is reasonably monochromatic and its spectrum contains several sharp emission energy lines at fixed wavelengths. The $NO_2$ absorbance usually is read at 546 nm. When the oxygen concentration and the resulting $NO_2$ concentration are low, it is practical to read absorbance at 436 nm. FIG. 2 shows the $NO_2$ absorbance at different wavelengths. It can be seen that the absorbance at 436 nm is much higher than the absorbance at 546 nm. Normally, a reference absorbance reading also is taken to compensate for any light scattering by particulate matter and mist in the gas sample. For this purpose, a wavelength is chosen at which light is absorbed less strongly. Thus, for determining absorbance at 436 nm, the reference reading can be taken either at 546 or 578 nm. For absorbance at 546 nm, the reference reading is taken at 578 nm. An optical calibration filter corresponding to a fixed $NO_2$ concentration can be used to calibrate the equipment.

The photometer is of the same type as that described in U.S. Pat. No. 3,718,429. The light beam transmitted through optical cell 7 is split into two by a semitransparent mirror. One half of the beam passes through a filter which blocks all but the measuring radiation (responsive to both $NO_2$ absorption and the light scattering). This radiation is positively amplified by a logarithmic amplifier. The second half of the light beam excludes all but the reference radiation. This is negatively amplified by a logarithmic amplifier, which subtracts the scattering value from the total absorption valve, thus leaving only the $NO_2$ absorption to reach control station 14. The schematic drawing and discussion of this photometer in U.S. Pat. No. 3,718,429 are incorporated herein by reference. The diagram in FIG. 1 of this disclosure substantially corresponds to that of FIG. 3 in U.S. Pat. No. 3,718,429, except that a cylinder of NO is substituted in the present arrangement for the oxygen tank. The general discussion of this equipment in U.S. Pat. No. 3,718,429 applies equally well to the present disclosure.

INSTRUMENT CALIBRATION

Oxygen concentration determinations were conducted according to the method of the present invention using Du Pont "461 $NO_x$ Analyzer system." The optical absorption cell was 38 cm long. Air was passed through the optical absorption cell; then the cell was sealed off, and NO was injected at a pressure of about 0.06 MPa. The absorbance due to $NO_2$ at 546 nm, compensated for scatter by subtracting reference absorbance at 578 nm, was read, and the recorder was adjusted for about 84% of full scale. Subsequently, absorbance values were determined for blends of air with nitrogen in respective volume ratios of 50:50 and 25:75. Excellent reproducibility and linearity of response were noted within this range, which corresponds to oxygen concentrations of 20.9 to 5.22 volume percent. It is readily apparent that linear response would also be obtained at lower concentrations, and that the 436 nm wavelength can be used for lower concentrations to increase the magnitude of absorbance.

Once $NO_2$ absorbance for one or more $NO_2$ concentrations has been determined as described above, it is possible to calibrate and check the equipment by using a series of optical filters corresponding to these experimentally determined absorbance values, without actually introducing oxygen and NO into the system. Meter or recorder data thus can be correlated with known $NO_2$ levels which correspond to defined oxygen levels.

I claim:

1. A method of monitoring oxygen concentration in a gas mixture, said method comprising the following steps:
   (1) passing at a predetermined pressure a sample of the gas to be analyzed through a leak-tight optical absorption cell having high transparency in the 325–600 nm range and maintained at a predetermined temperature above 100° C., said optical absorption cell being placed in the path of a visible light beam;
   (2) sealing off said optical absorption cell at said predetermined pressure;
   (3) establishing by means of a light detector the base absorbance of the gas to be analyzed or zeroing the light detector to eliminate said base absorbance;
   (4) introducing into said optical absorption cell nitrogen oxide, NO, at a pressure at least equal to twice the partial pressure of oxygen in the gas sample, within the range of 0.01 to 0.2 MPa;
   (5) determining the absorbance, at a predetermined wavelength within the 325–600 nm range, of nitrogen dioxide, $NO_2$, formed by reaction of oxygen with nitrogen oxide, NO; and
   (6) calculating the oxygen concentration in the gas sample from said absorbance;
   with the proviso that the above step (3) may be performed at any time prior to the introduction of nitrogen oxygen into the optical absorption cell, whether or not the cell is sealed off.

2. The method of claim 1 wherein the sample gas is passed through the optical absorption cell and the optical absorption cell is sealed at a subatmospheric pressure.

3. The method of claim 1 wherein the amount of NO introduced into the optical absorption cell is in excess over the stoichiometric requirement of the NO reaction with oxygen.

4. The method of claim 3 wherein the excess is about 100%.

5. The method of claim 1 wherein the temperature at which the optical absorption cell is maintained is about 105° C.

6. The method of claim 1 wherein the visible light source is a mercury vapor lamp.

7. The method of claim 1 wherein the light detector is a photometer.

* * * * *